(12) United States Patent
Rui et al.

(10) Patent No.: US 8,343,921 B2
(45) Date of Patent: Jan. 1, 2013

(54) METHOD FOR TREATING MYOCARDIAL ISCHEMIA

(75) Inventors: Yaocheng Rui, Shanghai (CN); Tiejun Li, Shanghai (CN); Pengyuan Yang, Shanghai (CN); Yuefan Zhang, Shanghai (CN)

(73) Assignee: Shanghai Bajiayi Pharmaceutical Science and Technology Co. Ltd., Shanghai (CN)

( * ) Notice: Subject to any disclaimer, the term of this patent is extended or adjusted under 35 U.S.C. 154(b) by 0 days.

(21) Appl. No.: 13/355,873

(22) Filed: Jan. 23, 2012

(65) Prior Publication Data

US 2012/0122786 A1 May 17, 2012

Related U.S. Application Data

(63) Continuation of application No. PCT/CN2010/075181, filed on Jul. 15, 2010.

(30) Foreign Application Priority Data

Jul. 23, 2009 (CN) .......................... 2009 1 0055203

(51) Int. Cl.
*A61P 9/10* (2006.01)
*A61K 38/08* (2006.01)
*C07K 7/06* (2006.01)

(52) U.S. Cl. ....................... 514/16.4; 514/21.8; 530/330

(58) Field of Classification Search ........................ None
See application file for complete search history.

(56) References Cited

FOREIGN PATENT DOCUMENTS

| CN | 101361961 A | 2/2009 |
| CN | 101612384 A | 12/2009 |
| WO | 00/00511 A1 | 1/2000 |

OTHER PUBLICATIONS

Machine translation of CN101361961, Yang et al, translated on Aug. 13, 2012 using toolkit.dialog.com, 5 pages as printed.*
Traystman. 2003. ILAR J. 44(2): 85-95.*
Bader, 2010. Chapter 27 of Rat Genomics: Methods and Protocols, Methods in Molecular Biology, 597: 403-414.*
Fisher et al, 2008. American Journal of Therapeutics. 15: 137-149.*
Liu et al., 1996, "Clinical Study on Treatment and Prevent of Cardiomuscular Ischemia Resulting from Cerebral Ischemia and ECG," Journal of Modern Electrophysiology, 3(4):193-197.
Li, 2004, "Inflammation Influence and Antiinflammation Therapeutic Effect of Sodium Diclofenac on Experimental Acute Myocardial Ischemia of Rabbits," Chinese Master's Theses Full-Text Database Medicine and Health Sciences, vol. 3.
PCT International Search Report for PCT/CN2010/075181 mailed Oct. 28, 2010.

* cited by examiner

*Primary Examiner* — Zachary Howard
(74) *Attorney, Agent, or Firm* — Sutherland Asbill & Brennan LLP

(57) ABSTRACT

Use of polypeptide micromolecule MLIF in preparing medicine for preventing and treating myocardial ischmia, where amino acid sequence of the polypeptide micromolecule MLIF is Met-Gln-Cys-Asn-Ser (SEQ ID NO:1).

5 Claims, No Drawings

```
                        SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Gln Cys Asn Ser
1               5
```

METHOD FOR TREATING MYOCARDIAL ISCHEMIA

CROSS REFERENCE TO RELATED APPLICATIONS

This application is a continuation of PCT/CN2010/075181 filed on Jul. 15, 2010, which claims priority benefit of Chinese Application No. 200910055203.X filed on Jul. 23, 2009. The entire contents of these applications are hereby incorporated in their entirety.

TECHNICAL FIELD OF THE INVENTION

The present invention relates to the technical field of biological medicine, more particularly to a new use of polypeptide micromolecule MLIF in preparing medicine for preventing and treating myocardial ischemia.

BACKGROUND OF THE INVENTION

Myocardial ischemia refers to a kind of pathological state that reduction of blood perfusion in heart causes reduced oxygen supply to heart, irregular energy metabolism of myocardium and abnormal work of heart. Clinical studies revealed that coronary artery stenosis, whose primary cause is arteriosclerosis, is the most major and common pathogenesis of myocardial ischemia. Coronary disease, what people often say, is heart disease caused by coronary atherosclerosis. At present, there are a lot of therapeutic regimes for myocardial ischemia which is a kind of coronary heart disease, such as stent placement and balloon dilation, whereas drug therapy is still a main method. Nitrate esters medicines (e.g. isosorbide mononitrate or its slow-release), beta blockers like propranolol and calcium channel blockers like nifedipine could be selected to dilate coronary arteries, increase myocardial oxygen supply, reduce peripheral resistance, working of heart and oxygen consumption of myocardium. Statins (e.g. atorvastatin, simvastatin) also should be taken to reduce plasma cholesterol and steady atherosclerotic plaque, preventing plaque from coming off to form thrombosis which causes stroke.

Inflammatory reaction plays important roles in the myocardial ischemia injury, whose main processes include the chemotaxis and infiltration of inflammatory-cells such as neutrophils, monocytes and lymphocytes etc., as well as the synthesis and secretion of inflammation factors. However, up till now, there is no clinical medicine for protecting myocardial ischemia by the anti-inflammatory mechanism. The monocyte locomotion inhibitory factor (MLIF), which is a polypeptide of anti-inflammatory reaction, is a pentapeptide found in sterile cultured amoeba histolytica, whose amino acid sequence is Met-Gln-Cys-Asn-Ser (SEQ ID NO:1). Experiment results in vitro and in vivo demonstrated that the pentapeptide MLIF inhibits the migration of human monocytes and polymorphonuclear neutrophils. Amoeba histolytica influences cytokines secretion, inhibits inflammation and escapes immune response of host by producing the anti-inflammatory polypeptide. It has been reported that the pentapeptide micromolecular not only directly affects inflammatory cells, but also influences the inflammatory reaction process by interfering inflammatory cytokines secretion. The MLIF also inhibits inflammation chemokines such as MIP-1α and MIP-1β, and represses inflammatory cytokines secretion like 1L-1β and TNF-α along with the corresponding receptor expression. In the study, the inventor found out that MLIF has the function of preventing and treating ischemic cerebrovascular disease, which has already applied for a patent application, e.g., CN 200810200610.0), but so far, there is no report about the function of the polypeptide in preventing and treating myocardial ischemia.

SUMMARY OF THE INVENTION

The present invention provided a new application of polypeptide micromolecule MLIF in preparing medicine for preventing and treating myocardial ischemia. In pharmacologic experiments of rat myocardial ischemia models induced by coronary artery ligation, the polypeptide micromolecule MLIF showed to reduce rat myocardial damage and myocardial infarction areas caused by myocardial, ischemia, providing that the polypeptide micromolecule MLIF has the function of preventing and treating myocardial ischemia. Thus, the polypeptide micromolecule MLIF can be used for preparing medicine for preventing and treating myocardial ischemia.

In certain embodiments, a composition comprising a therapeutic effective amount of polypeptide micromolecule MLIF with an amino acid sequence of Met-Gln-Cys-Asn-Ser (SEQ ID NO:1) for preventing and treating myocardial ischemia is provided. In other embodiments, the present invention also provides a method of preventing and treating myocardial ischemia using the polypeptide micromolecule MLIF with an amino acid sequence of Met-Gln-Cys-Asn-Ser (SEQ ID NO:1).

DETAILED DESCRIPTION OF THE INVENTION

Description for the invention is illustrated in detail below.

1 Polypeptide Micromolecule MLIF

The amino acid sequence is Met-Gln-Cys-Asn-Ser (SEQ ID NO:1). It was synthesized in more than 95% purity by Sangon Biotech (Shanghai) Co., Ltd.

2 Animal Experiments 2.1 Protection Effect for Rat Myocardial Infarction Area Caused by Acute Myocardial Ischemia 2.1.1 Experimental Animals Sprague-Dawley male rats of clean grade weighting 200-220 g were supplied by the animal experimental center of the Second Military Medical University (license number: SCXK (Shanghai)-2007-0003).

2.1.2 Experimental Groups

Experimental rats were randomly divided into four groups: sham group: n=8, model group: n=9, MLIF low-dose group: n=11, MLIF high-dose group: n=12. The dose of medicine could be administrated according to rat body weight. MLIf low-dose group and MLIF high-dose group were administrated by tail intravenous injection prepared with normal saline as solvent at the dose of 0.15 mg/kg and 0.5 mg/kg, respectively.

2.1.3 Coronary Artery Ligation and Measurement of Myocardial Infarction Area of Rats The Sprague-Dawley male rats were abdomen anesthetized with 25% urethane (0.4 ml/100 g) and fixated at supine position. The chest was cut open among the fifth rib at left, and then the fourth and fifth ribs were cut off along the left side of sterna at 2 mm. The pericardium was snipped off with heart exposed, and a 0/3 suture line was passed through the left anterior descending coronary artery. The rats were administrated by tail intravenous injection slowly. After 10 minutes, the left anterior descending coronary artery was ligated rapidly and the heart was returned to its chest, removing the air within the thorax by hand, closing the thorax and tightening the purse-string suture rapidly. The entire process of opening and closing chest was performed within 30 seconds. The coronary arteries of rats of sham group were not ligated since the myocardial ischemia would be caused by coronary artery ligation.

The rats were administrated by tail intravenous injection with the dose of 0.15 mg/kg (MLIF low-dose group) and 0.5 mg/kg (MLIF high-dose group) at 15 minutes after coronary artery ligation with the same volume of normal saline administrated in sham group and model group. Each group of animals was executed at 5 hours after coronary artery ligation. The heart was taken out and the heart ventricle muscle was transversely chipped into 5 slices, the cut position of which was parallel to coronary sulcus under the coronary artery ligation line. The five slices of the heart ventricle muscle were stained with Nitroblue tetrazolium (N-BT) for 15 minutes with shaking. The normal heart ventricle muscle was dyed into dark blue while that of the area of myocardial infarction was unstained with normally light yellow. The area of myocardial infarction was isolated by a dissecting microscope and the whole heart weight, the left ventricle weight and the area of myocardial infarction weight were weighed, respectively, the percent (%) of area of myocardial infarction weight to whole heart weight were quantified as an measure on myocardial infarction area ranges.

2.1.4 Data and Statistics Analysis

All experimental data are given as $_x\overline{\phantom{x}}\pm SD$. Differences between the groups were calculated by analysis of variance (SPSS 10.0). Results are shown in Table 1.

TABLE 1

Effect of polypeptide MLIF on myocardial ischemia injury of rats treated with coronary artery ligation ($\overline{x} \pm SD$)

| | Groups | | | |
|---|---|---|---|---|
| | sham group | model group | MLIF low-dose group | MLIF high-dose group |
| Numbers of rats | 8 | 9 | 11 | 12 |
| whole heart weight (mg) | 728 ± 58 | 763 ± 45 | 832 ± 63.5 | 779 ± 51.2 |
| left ventricle weight(mg) | 497 ± 36 | 532 ± 33.1 | 566 ± 48.1 | 526 ± 31.5 |
| area of myocardial infarction weight (mg) | 0 ± 0 | 201 ± 37.4$^{\Delta\Delta}$ | 187 ± 22.8$^{\Delta\Delta}$ | 158 ± 22.4$^{\Delta\Delta}$ |
| area of myocardial infarction/ whole heart (%) | 0 ± 0 | 26 ± 4.1$^{\Delta\Delta}$ | 22 ± 1.9$^{\Delta,*}$ | 20 ± 2.7$^{\Delta\Delta,**}$ |
| area of myocardial infarction/ left ventricle (%) | 0 ± 0 | 38 ± 6$^{\Delta\Delta}$ | 33 ± 3.2$^{\Delta\Delta,*}$ | 30 ± 3.7$^{\Delta\Delta,**}$ |

$^{\Delta}P < 0.05$,
$^{\Delta\Delta}P < 0.01$ vs sham group;
$*P < 0.05$,
$**P < 0.01$ vs model group As shown in Table 1, after 5 hours of rats ischemia caused by coronary artery ligation, the ratios of infarction area to whole heart and left ventricle in the model group were 26±4.1% and 38±6%, respectively, with a great difference compared to sham group (P<0.01). The ratios of infarction area to whole heart and left ventricle in the MLIF high-dose group (0.5 mg/kg) were 20±2.7% and 30±3.7%, respectively, with a great difference compared to the model group (P<0.01). The ratios of infarction area to whole heart and left ventricle in the MLIF low-dose group were 22±1.9% and 33±3.2%, respectively, with a difference compared to the model group (P<0.05). It was suggested that the polypeptide micromolecule MLIF reduced rat myocardial damage and myocardial infarction areas induced by myocardial ischemia, which proved that it has the function of protecting myocardial ischemia injury.

2.2 Effect on Serum Creatine Kinase (CK) and Lactic Dehydrogenase (LDH) of Acute Myocardial Ischemia Rats 2.2.1 Experimental Animals Sprague-Dawley male rats of clean grade weighting 200-220 g were supplied by the animal experimental center of the Second Military Medical University (license number: SCXK (Shanghai)-2007-0003).

2.2.2 Experimental Groups

Experimental rats were randomly divided into four groups: sham group: n=7, model group: n=8, MLIF low-dose group: n=8, MLIF high-dose group: n=9. The dose of medicine could be administrated according to rat body weight. MLIF low-dose group and MLIF high-dose group were administrated by tail intravenous injection prepared with normal saline as solvent at the dose of 0.15 mg/kg and 0.5 mg/kg, respectively.

2.2.3 Coronary Artery Ligation and Determination of CK and LDH in Blood Serum

Coronary artery ligations of rats were carried out as described previously. 3 ml blood sample of each animal was taken from femoral artery at 5 hours after coronary artery ligation and the blood serum was collected according to the method of convengtional centrifugalization. The creatine kinase (CK) and lactic dehydrogenase (LDH) activities in blood serum were measured by semi-automatic biochemical analyzer.

2.2.4 Data and Statistics Analysis

All experimental data are given as $_x\overline{\phantom{x}}\pm SD$. Differences between the groups were calculated by analysis of variance (SPSS 10.0). Results are shown in Table 2.

As shown in Table 2, cardiomyocytes of rats were injured by myocardial ischemia after coronary artery ligation. And then, LDH and CK in cells were released into blood, resulting in an increase of LDH and CK in blood serum. In rats of the model group, the LDH and CK activities were 4736±755.7 IU/L and 7680±2380 IU/L, respectively, with a significant difference compared to the sham group (P<0.01). The LDH and CK activities in blood serum were 3642±817 IU/L (P<0.01) and 5244±1787.8 IU/L (P<0.05) in the rats of the MLIF high-dose group (0.5 mg/kg), respectively. At the same time, the LDH and CK activities in blood serum were 3156±864.1 IU/L (P<0.01) and 5258±2114.3 IU/L (P<0.05) in the rats of the MLIF low-dose group (0.15 mg/kg), respectively. The results indicated that the polypeptide micromolecule MLIF can reduce the contents of LDH and CK in blood serum of myocardial ischemia rats, which proved that it has the function of protecting myocardial ischemia injury.

TABLE 2

Effect of polypeptide MLIF on serum creatine kinase (CK) and lactic dehydrogenase (LDH) in acute myocardial ischemia rats ($\overline{x} \pm SD$)

| Groups | Numbers of rats | CK (IU/L) | LDH (IU/L) |
|---|---|---|---|
| sham group | 7 | 2633 ± 344.9 | 1226 ± 421.3 |
| model group | 8 | 7680 ± 2380$^{\Delta\Delta}$ | 4736 ± 755.7$^{\Delta\Delta}$ |
| MLIF low-dose group | 8 | 5258 ± 2114.3$^{\Delta\Delta,*}$ | 3156 ± 864.1$^{\Delta\Delta,**}$ |

TABLE 2-continued

Effect of polypeptide MLIF on serum creatine kinase (CK) and lactic dehydrogenase (LDH) in acute myocardial ischemia rats ($\bar{x} \pm SD$)

| Groups | Numbers of rats | CK (IU/L) | LDH (IU/L) |
|---|---|---|---|
| MLIF high-dose group | 9 | $5244 \pm 1787.8^{\Delta\Delta,*}$ | $3642 \pm 817^{\Delta\Delta,**}$ |

$^{\Delta}P < 0.05$,
$^{\Delta\Delta}P < 0.01$ vs sham group;
$^{*}P < 0.05$,
$^{**}P < 0.01$ vs model group The above-mentioned results showed that MLIF with the concentration of 0.15 mg/kg and 0.5 mg/kg reduced the content of LDH and CK in blood serum, as well as the rat myocardial infarction areas induced by coronary artery ligation, indicating that it has the function of protecting myocardial ischemia injury. Thus, the MLIF can be applied to prepare medicine for preventing and treating myocardial ischemia.

What is claimed is:

1. A method for treating myocardial ischemia comprising administering to a patient in need thereof an effective amount of a MLIF peptide having the amino acid sequence of Met-Gln-Cys-Asn-Ser (SEQ ID NO: 1).

2. The method of claim 1, wherein said administration reduces myocardial damage caused by said myocardial ischemia.

3. The method of claim 1, wherein said administration reduces the area of myocardial infarction caused by said myocardial ischemia.

4. The method of claim 1, wherein said administration reduces an amount of creatine kinase (CK) in blood serum generated by said myocardial ischemia.

5. The method of claim 1, wherein said administration reduces an amount of lactic dehydrogenase (LDH) in blood serum generated by said myocardial ischemia.

* * * * *